United States Patent
Giraud-Guille et al.

(10) Patent No.: US 9,867,902 B2
(45) Date of Patent: Jan. 16, 2018

(54) DENSE FIBRILLAR COLLAGEN MATRICES FOR TISSUE REPAIR AND THE PREPARATION METHOD THEREOF

(75) Inventors: Marie-Madeleine Giraud-Guille, Paris (FR); Nadine Nassif, Paris (FR); Yan Wang, Paris (FR); Christophe Helary, Champigny sur Marne (FR); Anne Pelle, Vanves (FR)

(73) Assignees: UNIVERSITE PIERRE ET MARIE CURIE (PARIS 6), Paris (FR); CENTRE NATIONAL DE LA RECHERCHE SCIENTIFIQUE, Paris (FR); UNIVERSITE DE VERSAILLES SAINT QUENTIN EN YVELINES, Versailles (FR)

(*) Notice: Subject to any disclaimer, the term of this patent is extended or adjusted under 35 U.S.C. 154(b) by 0 days.

(21) Appl. No.: 13/701,071

(22) PCT Filed: May 30, 2011

(86) PCT No.: PCT/FR2011/051234
§ 371 (c)(1),
(2), (4) Date: Feb. 1, 2013

(87) PCT Pub. No.: WO2011/151587
PCT Pub. Date: Dec. 8, 2011

(65) Prior Publication Data
US 2013/0142840 A1    Jun. 6, 2013

(30) Foreign Application Priority Data
May 31, 2010 (FR) ...................................... 10 54194

(51) Int. Cl.
*A61L 27/24* (2006.01)
*A61L 27/18* (2006.01)

(52) U.S. Cl.
CPC .............. *A61L 27/24* (2013.01); *A61L 27/18* (2013.01); *A61L 2430/40* (2013.01)

(58) Field of Classification Search
CPC ...................... A61L 27/24; A61F 2310/00365
See application file for complete search history.

(56) References Cited

U.S. PATENT DOCUMENTS

| 4,018,826 A | * | 4/1977 | Gless et al. | 525/418 |
| 5,256,418 A | * | 10/1993 | Kemp | A61L 27/24 424/422 |
| 2009/0054350 A1 | | 2/2009 | Tayot | |

FOREIGN PATENT DOCUMENTS

| EP | 0 457 430 | 11/1991 |
| WO | 2006/029571 | 3/2006 |
| WO | 2010/004182 | 1/2010 |

OTHER PUBLICATIONS

Giraud Guille et al., Soft Matter, 2010, 6, 4963-4967.*
Strasser, Dissertation, Sep. 1, 2007, 1-83.*
Of Zeugolis et al., J. Biomedical Materials Research, Part B, 85B, 2008, 343-352.*
Dulbecco's PBS, 1 page, 2005.*
International Search Report dated Dec. 5, 2011, corresponding to PCT/FR2011/051234.

* cited by examiner

*Primary Examiner* — Kyle Purdy
(74) *Attorney, Agent, or Firm* — Young & Thompson

(57) ABSTRACT

Method for preparing a homogeneous collagen-based material by concentration of a collagen solution, includes bringing a collagen solution into contact by way of continuous injection and use of the material for tissue repair.

8 Claims, 14 Drawing Sheets

A

B

FIGURE 2 (CONTINUATION)
C
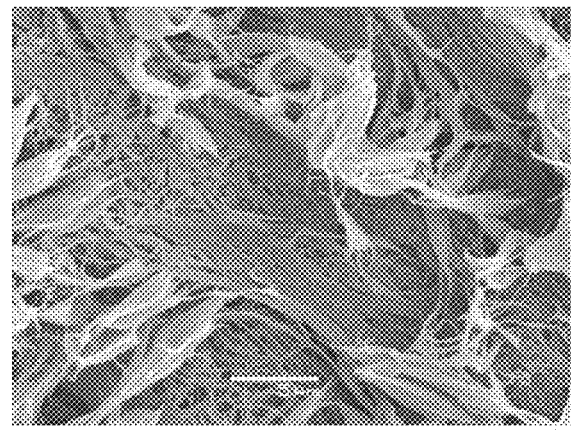
D
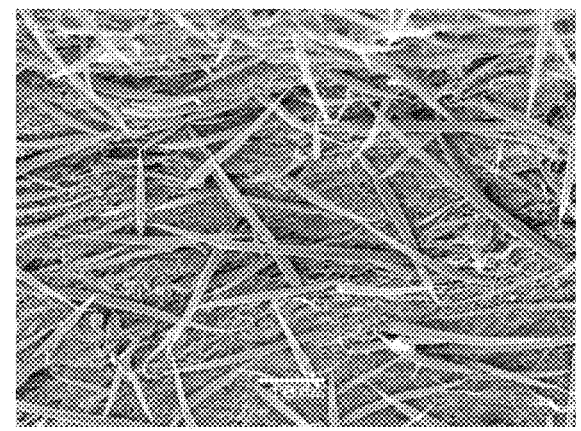

A

B

FIGURE 4 (CONTINUATION)
C
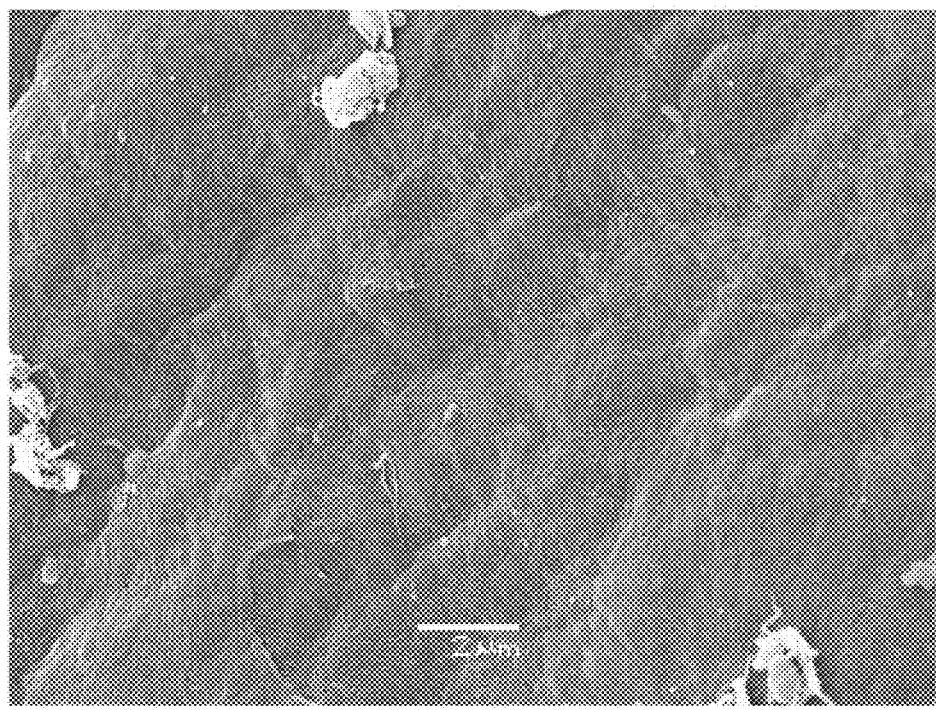
D
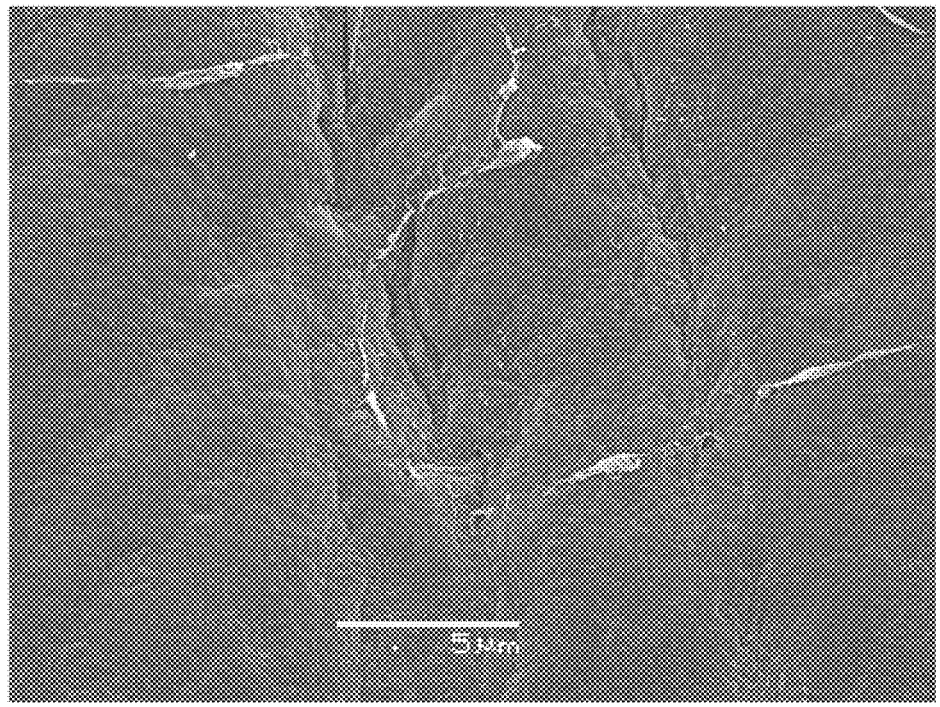

A

B

A

DM20

B

DM40

DENSE FIBRILLAR COLLAGEN MATRICES FOR TISSUE REPAIR AND THE PREPARATION METHOD THEREOF

A subject of the present invention is a method for the preparation of dense fibrillar collagen matrices, the matrices thus obtained and uses thereof for tissue repair.

I—CURRENT SITUATION AND EXPECTATIONS

Biomaterials are important to meeting the economic and social challenges caused by the significant increase in life expectancy in Western countries, and associated pathologies.

Numerous substitute materials, of a synthetic nature (metals, ceramics, polymers) or natural (chitosan, dextran, pullulan), glycoaminoglycans (GAGs) or collagen) are proposed in the literature. The quality criteria of the biomaterials are determined by their ease of use, their mechanical properties and their fate in the organism (rejection or degradation, adhesion and cell colonization, remodelling).

Thus in the present context, different types of collagen-based substitutes are already proposed at industrial application level, however they still fail to meet fully the expectations of surgeons and patients.

The first collagen-based biomaterials having led to industrial applications, related to skin substitutes. The products marketed have been proposed as implants for serious burn patients or dressings for chronic wounds and ulcers. The first dermal substitute, sold under the name of Integra®, is an acellular sponge of collagen and proteoglycans bridged with glutaraldehyde. Combined with a keratinocyte sheet, marketed under the name of Epicel®, the dermal equivalent becomes a skin substitute.

In other applications the substitutes include polymers of synthetic origin or incorporate cells and their success will depend on cell/matrix interrelations. The adhesion of the cells in large pores, within lyophilized collagen sponges (Orcel® or Integra®) places them in a situation where the support is 2D, in this case the phenotype differs from the in vivo situation where the cells have 3D contacts. This reinforces the advantage of the molecules of natural origin, in particular collagen, in promoting adhesion and cell colonization. The only systems where the fibroblasts are found with 3D contacts are the collagen hydrogels developed in the United States. These hydrogels combined with keratinocyte sheets then become cutaneous repair materials (Apligraf®). The major drawback of these biomaterials resides in their poor mechanical properties.

The collagen-based materials which can be implanted at present are derived from two production processes, leading either to sponges or to hydrogels. These basic materials are then subjected to treatments which will reinforce the quality of the commercial products by combination with chemical molecules (consolidation), cells (fibroblasts) or protective films (silicone). The collagen sponges, obtained by lyophilization of acid-soluble collagen solutions are porous three-dimensional systems. The size of the pores, from 15 to 150 µm in diameter, varies according to the criteria of freezing prior to lyophilization. The sponge structure allows the seeded fibroblasts to proliferate by colonizing the entire substrate and then to secrete fibrillar collagen. The uses of these systems in cell or gene therapy are linked to their biocompatible and biodegradable support properties. However the fragility of the sponges and their short lifespan in the organism requires cross-linking by chemical agents (aldehydes, carbodiimides) the toxicity of which poses problems. The collagen hydrogels are obtained by precipitation of the collagen monomers to form fibrils within an acid-soluble solution. When fibroblasts are combined with the starting solution and culture medium, fibrillar gel which is weakly concentrated (~1 mg/ml) and random in structure traps the cells. A significant contraction of the gel is then observed over the next few days (~3% of initial surface after 14 days in culture) and results in what is known as a dermal equivalent. This reconstituted tissue becomes a skin equivalent when it is secondarily seeded by cells of the epidermis, keratinocytes, which proliferate and cover the structure. Although grafting trials in humans have demonstrated the biological qualities of these substitutes, the contraction phenomena of the loose fibrillar network however pose obvious problems of fragility, during the handling of the materials or after their implantation. These hydrogels have been the subject of numerous remodelling (synthesis of collagen and metalloproteinases) and cell proliferation studies. Whilst the hydrogels are useful cell culture models, they have proved inadequate as substrates for tissue repair. The mechanical properties of the hydrogels have been improved by increasing their concentration by compression (cf. §II.4), then resulting in easily dehydrated and friable films; their thickness, which is of the order of 40 µm, is too fine for many applications.

In parallel, decellularized biological tissues of animal origin (heart valves, vessels, dermis, connective tissues of bovine or porcine origin), combined with other components, have been put on the market. In this type of approach, complications linked to the preparation methods (residual cell debris or cytotoxicity linked to the cross-linking agents) indicate significant inflammatory reactions and have serious consequences in terms of morbidity and mortality.

There is therefore a need for new biomaterials which correspond better to the expectations of medical professionals and patients, in particular biomaterials free of toxicity, in various forms or for covering materials, which can be colonized by cells and incorporated into the host's tissues.

The inventors have developed techniques making it possible to work with collagen at high concentrations, by controlling the establishment of a supramolecular order linked to the concentration and by stabilizing during a sol/gel transition leading to dense fibrillar matrices. REDThe inventors have also demonstrated that matrices with 40 mg/ml of collagen have particularly useful properties in terms of their cell and mechanical responses. They are colonized in vitro by fibroblasts seeded in their surface following the hydrolysis of the collagen via metalloproteases. After culture for 28 days the number of cells present within the matrix, resulting from a balance between proliferation and apoptosis, is similar to that of a living tissue (Helary et al. Biomaterials, (2005), 26 p. 1533-1543; Helary et al. Biomaterials (2006) 27: 4443-4454. The mechanical responses under uniaxial compression produce results equivalent to control samples of rat dermis suggesting that these materials could be used in tissue repair (Ramtani et al. JMMB, 2010).

The Application WO 2010/004182 in the name of the inventors relates to the mineralization of these dense fibrillar collagen matrices in a higher concentration range (starting from 80 mg/mL) for use in the field of bone substitutes.

In previous works, the inventors used different methods for concentrating the collagen with the objective of obtaining a dense fibrillar collagen matrix.

II—PREVIOUS METHODS FOR OBTAINING DENSE MATRICES

1) Evaporation

Method—The initial acid solutions of collagen, the initial concentration of which is less than 5 mg/mL, are placed in a crystallizing dish (or any other broad open container) under a hood in a sterile environment. The solution is left to evaporate until the desired concentration is reached (Helary et al. Biomaterials, 2005).

Limits—This technique is not suitable for very high concentrations and high volume. In fact, starting with an initial solution of 1 mg/mL in order to obtain a 300 mg/mL solution, a very large and, as previously mentioned, very broad container is required so as not to have to wait a significant time to recover the sample. Furthermore a film of dry collagen can form on the surface. Moreover after precipitation by raising the pH, the collagen fibrils are not always homogeneous in size. This technique cannot be readily adapted/transferred to industry as it would require a large sterile area due to the use of an open vat. Moreover, at very high concentrations or, even more so, in the case of large volumes, a concentration gradient forms (more concentrated area at the surface i.e. at the air/solution interface) and it seems difficult to reach equilibrium. The existence of this gradient partly explains why the collagen fibrils are not always homogeneous in size.

2) Dialysis

Method—The acid solutions of collagen the initial concentration of which is less than 5 mg/mL are placed in dialysis tubing. The porosity of the membrane is fixed so that the solvent, the salts and the molecules the molecular weight of which is less than the size of the pores diffuse through the wall but not the collagen. The whole is immersed in a polymer solution (in general polyethylene glycol or PEG) the concentration of which is equal to/or slightly greater than that desired (Gobeaux et al. J. Mol. Biol. 2008).

Limits—With this technique, starting from an initial solution of 1 mg/mL in order to obtain a 300 mg/mL solution, a volume of membrane at least equal to 300 mL is required in order to obtain a final volume of 1 mL of concentrated solution, which is not experimentally obvious. Also, in general smaller volumes of dialysis membranes are used, with regular reloading with collagen, until a fairly consistent volume of solution is obtained in order to allow extraction. This stage also poses problems as it is then necessary to "scrape" the concentrated collagen which has spread thinly all over the inside of the membrane which, due to shearing, risks modifying the organization of the collagen which at this concentration possesses organization properties of the crystal-liquid type. Therefore it is difficult to control the final organization. Because of this, after precipitation by raising the pH, the collagen fibrils are not homogeneous in size. Furthermore, the concentrated collagen solution recovered is not macroscopically homogeneous (see FIG. 1B), therefore the mechanical properties of the final material are not constant for all of the material.

3) Microcells

Method—The initial acid solutions of collagen are injected and progressively concentrated in glass microchambers produced in the laboratory. The principle is that diluted collagen is injected between slide and slip cover, which, by diffusing towards the edges of the microchamber to the interface with the air, gradually becomes concentrated by evaporation of the solution. The closer towards the edges of the microchamber (towards the air/solution interface) the more concentrated the collagens. A very significant concentration gradient of the collagen (~5 to 1000 mg/mL) forms within the final concentrated solution (G. Mosser et al., Matrix Biol. 2006).

Limits—There is therefore no control of the concentration. This method is useful for studying phase diagrams and is suitable for small volumes (less than 0.5 mL). However, the first layer at the air/solution interface is in reality a diluted layer as the collagen does not have time to become concentrated, and therefore organized, unlike the subsequent layer. After precipitation by raising the pH, the collagen fibrils are therefore not homogeneous in size here.

4) Compression

Method—This method proposes the compression of hydrated fibrillar collagen gels in order to obtain dense matrices. The fibrillar networks remain isotropic but the mechanical properties are far superior to those of the initial gel. The viability of cells inserted within such matrices, in the form of rolled sheets, has been verified (Brown et al. 2005).

Limits—The method is ultra-rapid and the collagen concentrations can reach 170 mg/mL. However the hydrogel is subjected to strong shearing and, due to its utilization, is extremely dehydrated which makes it fragile and subject to infections once implanted.

The limits of these previous methods demonstrates the major benefit, for tissue engineering applications, of having a methodology which makes it possible to obtain collagen matrices which are macroscopically homogeneous as regards concentration, fibril diameter and the order of which is controlled.

III—NOVEL METHOD FOR OBTAINING DENSE AND HOMOGENEOUS COLLAGEN MATRICES

The inventors have therefore developed a method making it possible to obtain dense fibrillar collagen matrices obtained at concentrations 5 to 60 times higher than the standard hydrogels, or even higher and containing no additive aimed at reinforcing the mechanical properties but only reconstituted pure collagen in the form of fibrils and dense fibril networks, which avoids inflammation, toxicity and rejection phenomena. The matrices obtained can be colonized by cells of the conjunctive tissue and their mechanical properties are similar to those of biological tissues.

A subject of the present invention is also a method for preparing a homogeneous collagen-based material starting with the concentration of an acid-soluble collagen solution, said method comprising:
  a) bringing into contact, by continuous injection of a collagen solution by controlled pressure means with a permeable element said permeable element itself being in contact with a concentrating agent such as a polymer solution
  b) keeping the collagen solution, permeable element and polymer solution in contact, under conditions allowing the selective mass transfer of the solvent contained in the aqueous solution of collagen in order to obtain the formation of a more concentrated solution of homogeneous collagen inside the permeable element or on the surface of the permeable element.

According to the invention, the permeable element is chosen with a pore size of molecular weight (MW) less than that of the collagen on the one hand and of the external polymer on the other hand. Keeping the collagen solution separated from the polymer solution by the permeable element in contact, allows the solvent to diffuse internal collagen solution towards the external polymer solution. This makes it possible to obtain the formation of a more concentrated solution of homogeneous collagen inside the permeable element or on the surface of the permeable element by this selective transfer of solvent. In an advantageous embodiment of the invention, in order to allow the selective mass transfer of the solvent contained in the aqueous collagen solution, the osmotic pressure of the polymer solution is greater than that of the collagen solution.

The continuous injection by controlled means can be carried out by any system known to a person skilled in the art capable of allowing this type of injection, in particular an electric syringe pump or a pump. The injection rate is adapted so that the pressure force on both sides of the membrane is identical; thus the flow is adapted as a function of the polymer and its viscosity so that a person skilled in the art finds the rate avoiding the retraction of the membrane or its inflation until it punctures. The rate depends on the type of polymer used and its molecular weight, which is greater than the pores of the membrane. The adaptation of the rate lies within the general knowledge of a person skilled in the art. By way of example with PEG of a molecular weight of 35 KDa, it is possible to use a rate comprised between 1 and 15 µl/min which makes it possible to terminate the formation of the material after 15 days in the case of an injected 28 mL of a 1 mg/mL solution. The injection can be interrupted in order to reach equilibrium (i.e. when the collagen concentration is then homogeneous throughout the mould) more quickly and therefore reduce the concentration gradient more quickly and resumed in order to develop a multi-layer system of controlled concentration and of flexible organization. It is also possible to interrupt the injection without waiting for equilibrium which makes it possible to have a continuous concentration gradient.

An example of a device which can be used to implement the method of the invention is illustrated in FIG. 3.

In an advantageous embodiment of the method of the invention, the permeable element is a dialysis cell and said method comprises the following stages:
 a) preparation of an acid solution of pure collagen in an aqueous solvent,
 b) continuous injection of the pure collagen solution by controlled pressure means, into dialysis cells at least one of the ends of which is closed by a dialysis membrane the porosity of which is fixed so that only the solvent as well as the acid and any additives (such as collagens of different types, ions, mineral phase precursors (calcium, phosphate salts, etc.), glycosaminoglycans or organic molecules), if they are present, diffuse through said membrane, said membrane being in contact with a polymer solution, the concentration of which is adapted to the final collagen concentration,
 c) keeping the collagen solution, dialysis cell and polymer under conditions allowing the selective mass transfer of the solvent contained in the aqueous collagen solution in order to obtain the formation of pure homogeneous concentrated collagen solution in the dialysis cell or on the surface of the dialysis membrane,
 d) recovery of the mould in which the material is contained or of the membrane on the surface of which the homogeneous pure collagen material is fixed.

Within the meaning of the present invention, by pure collagen solution is meant a solution containing no compound added only for the purpose of reinforcing the final mechanical properties of the material; it is in particular free of cross-linking agents such as aldehydes and synthetic reinforcing polymers such as polyesters or natural reinforcing polymers such as chitosan. On the other hand, additives like molecules of interest such as agents making it possible to modify its porosity or the surface fillers of the collagen can be added to the material.

The collagen used in the present invention can be of natural or recombinant origin. It can in particular originate from the skin or tendons from where it is extracted by acid or enzymatic route according to techniques known to a person skilled in the art.

Within the meaning of the invention, the dialysis cell, at least one of the ends of which is closed by a dialysis membrane, can also be a mould constituted entirely by a dialysis membrane. In the case where a large quantity is injected so as to fill the mould, the collagen matrix is produced over the entire surface of the mould and not only on the membrane placed at the end. Thus the form of the dialysis element will determine the final form of the material if it is completely filled. The product can therefore be formulated as a function of thickness and concentration in the form of film, flexible membrane, tube or moulded for the purpose.

The acid solutions of collagen used in stage a) are prepared by techniques known to a person skilled in the art from natural or recombinant collagen. The aqueous solvent, advantageously acetic acid at a concentration comprised between 17 and 500 mM can contain different additives such as for example inorganic salts, other types of collagen or glycosaminoglycans such as sulphated heparin.

In an advantageous embodiment of the invention, the collagen concentration of the initial solution used in stage a) is comprised between 0.01 and 5 mg/ml, advantageously comprised between 0.5 and 3 mg/ml.

According to the invention, the polymer used can be any water-soluble polymer in acid medium, the molecular weight of which is greater than the size of the pores of the permeable element. It is in particular chosen from the group comprising Dextran® and polyethylene glycol (PEG). Advantageously the polymer is polyethylene glycol the molecular weight of which is greater than that of collagen, therefore greater than 3000 Da.

The concentration of the polymer solution can vary according to the case and its adjustment is within the capability of a person skilled in the art. If the volume of polymer solution is very large then the volume of solvent originating from the collagen solution is negligible and dilutes the polymer solution negligibly. In this case, the concentration of initial polymer is equal to the final collagen concentration. If the volume of polymer solution is not large and the initial polymer concentration equal to the final collagen concentration, the polymer solution is changed regularly so as not to slow down the diffusion. If the volume of polymer solution is not large and that of the initial polymer concentration is greater than the final collagen concentration, then the initial polymer concentration is calculated such that after dilution by the volume of solvent originating from the collagen solution, it is equal to the desired final collagen concentration.

IV—FIBRILLOGENESIS OF THE CONCENTRATED SOLUTIONS

According to the invention, before or after stage d), the method can moreover include a stage of formation of fibrils in the pure collagen material. The formation of these fibrils makes it possible to mimic the fibrillar structure of the collagen of the biological tissues.

The formation of the fibrils is carried out by any technique known to a person skilled in the art, in particular by neutralization of the solution based on homogeneous pure collagen by a gas (basic) or liquid (basic or neutral) phase. It can be done either in situ by replacing the polymer with the gas or liquid phase, which allows a "one-pot" preparation of the fibrillar collagen, or by immersion of the collagen material in a gas or liquid phase.

The method of the invention can also be implemented in order to produce multi-layer products by interrupting the injection. The injection can be interrupted in order to reach equilibrium more quickly and resumed in order to make different non-continuous concentration layers. It is also possible to stop the injection and not to wait for equilibrium in order to have different continuous concentration layers.

A subject of the invention is also a homogeneous material based on pure collagen capable of being obtained by a method as defined previously.

The product obtained according to the invention can be easily handled without tearing and sutured without additional cross-linking. It is homogeneous and has no variation in concentrations.

They do not trigger any inflammatory reaction at the implantation site and become incorporated into the tissues.

According to the invention materials are obtained, the concentration of which is approximately 5 to approximately 1000 mg/mL, in particular 5, 10, 20, 30, 40 and 250 mg/mL. For a concentration of 5 mg/mL, the elastic modulus is approximately 974±239 Pa and the viscous modulus is approximately 145±40 Pa. For a concentration of 10 mg/mL, the elastic modulus is approximately 1287±158 Pa and the viscous modulus is approximately 124±12 Pa. For a concentration of 20 mg/mL, the elastic modulus is approximately 2809±336 Pa and the viscous modulus is approximately 263±48 Pa. For a concentration of 40 mg/mL, the elastic modulus is approximately 9254±1032 Pa and the viscous modulus is approximately 786±46 Pa. The elastic and viscous modulus values are measured at 1 Hz and 2% deformation.

Depending on the collagen concentration and the thickness of the material according to the invention, it can therefore be used as tissue substitute, in particular as wall reinforcement, for producing prostheses, as soft tissue substitute or as filling material.

A subject of the invention is therefore also implantable medical devices characterized in that they comprise a material according to the invention. The invention is better understood in the light of Examples 1 to 3 and FIGS. 1 to 12 which illustrate it.

FIG. 1 represents A: an acid-soluble collagen solution at a concentration less than 5 mg/mL; B: concentrated collagen solution after dialysis; C: concentrated collagen solution according to the method of the invention.

FIG. 2 represents a collagen (acid-soluble) (final concentration ~200 mg/mL) obtained by dialysis which is macroscopically inhomogeneous (FIG. 2A). After neutralization, the size of the fibres observed by scanning electron microscopy is inhomogeneous (FIGS. 2B to 2D). The initial acid-soluble collagen concentration is approximately 3 mg/mL.

FIG. 3 shows an example of a device used according to the invention. In case 1, the entire volume of the dialysis cell is filled and concentrated homogeneously, in case 2, the injection is stopped for a time T so that all of the solution present in the cell is concentrated homogeneously.

FIG. 4 represents a collagen (acid-soluble) (final concentration ~250 mg/mL) obtained according to the technique of the invention which is macroscopically homogeneous (FIG. 4A). After neutralization, the size of the fibres observed by scanning electron microscopy is homogeneous (FIGS. 4B to 4D) and is organized (cholesteric geometry) with a large-scale homogeneity of structure (Figure B). The initial acid-soluble collagen concentration is approximately 1 mg/mL.

EXAMPLE 1: PREPARATION OF THE MATERIAL ACCORDING TO THE INVENTION AND CHARACTERIZATION 1.1. Preparation of the Initial Collagen Solutions A type I collagen is prepared from the tails of young Wistar rats, according to the following procedure. The rat tail tendons are excised in a sterile laminar flow hood, then washed in a phosphate buffered saline solution containing 137 mM of NaCl, 2.68 mM of KCl, 8.07 mM of $Na_2HPO_4$, and 1.47 mM of $NaH_2PO_4$, in order to remove the cells and the traces of blood. The tendons are then soaked in a 4 M NaCl solution in order to remove the remaining intact cells and precipitate a portion of the proteins with a high molecular weight. After a new washing with the buffered saline solution, the tendons are dissolved in a 500 mM aqueous acetic acid solution. The solution thus obtained is clarified by centrifugation at 41000 g for 2 h. The proteins other than the type I collagen are selectively precipitated in a 300 mM aqueous NaCl solution, then removed by centrifugation at 41000 g for 3 h. The collagen is recovered from the supernatant by precipitation in a 600 mM aqueous NaCl solution followed by centrifugation at 3000 g for 45 mM The pellets thus obtained are dissolved in a 500 mM aqueous acetic acid solution, then carefully dialysed in the same solvent in order to completely remove the NaCl. The solutions are kept at 4° C. and centrifuged at 41000 g for 4 h before being used.

Figure 1:
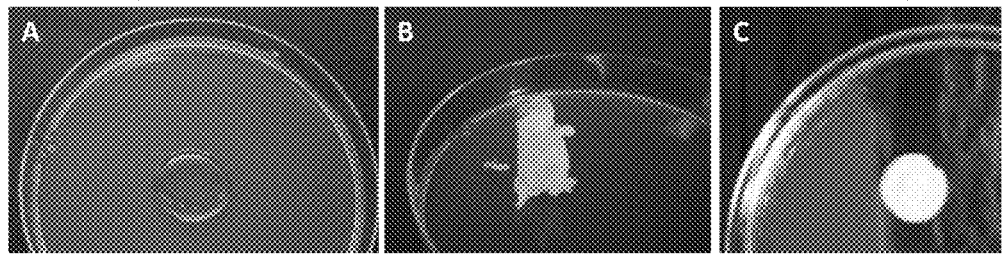

1.2. Preparation of the Homogeneous Material 18 ml of a collagen solution at a concentration of 3.2 mg/ml is introduced into a dialysis element equipped with an electric syringe pump as described in FIG. 1. The injection rate is fixed at 2 μl/min. The dialysis is carried out at 19° C.

in the presence of 150 ml of a 500 mg/mL solution of polyethylene glycol with a molecular weight of 35 kDa dissolved in a 500 mM aqueous acetic acid solution. The injection time is 8 days followed by stopping for 4 days in order to reach equilibrium. The collagen concentration of the acid solution as determined before fibrillogenesis by determination of the quantity of hydroxyproline is ~250 mg/mL.

The fibrillogenesis is carried out by immersion of the collagen material under ammonia vapour for 24 hours.

1.3. Measurement of the Homogeneity of the Material Obtained

Figure 2:
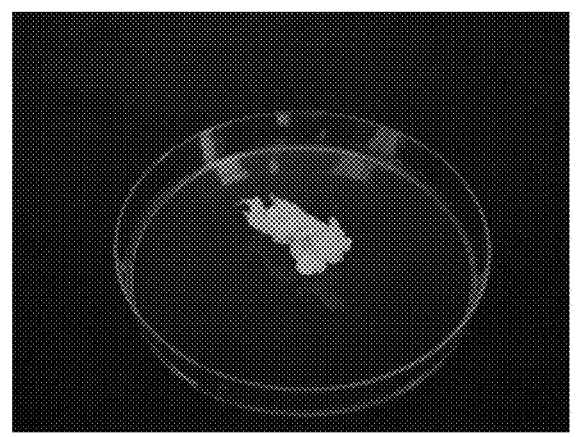
Figure 2:
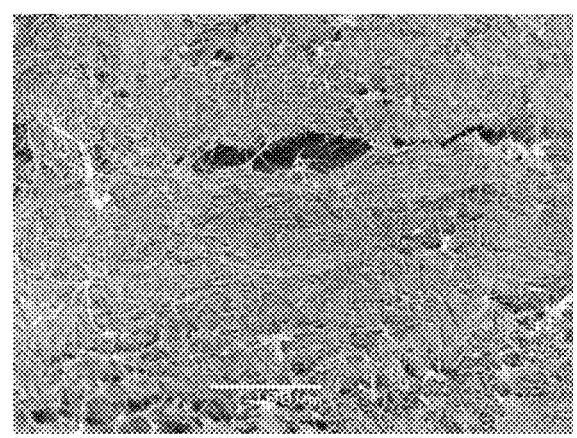
Figure 3:
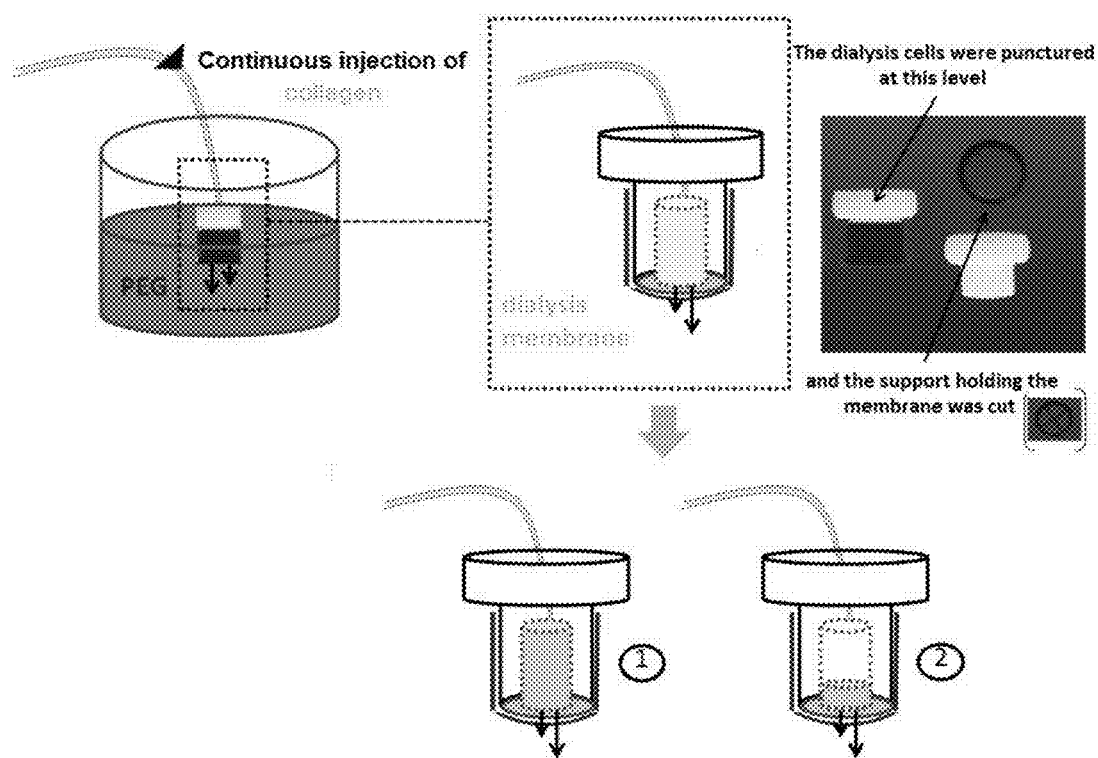

Using a scanning electron microscope, samples of material are observed, obtained from a solution having an initial concentration of acid-soluble collagen ~1 mg/mL (FIG. 3), either according to the standard reverse dialysis technique, or according to the method of the invention having an initial acid-soluble collagen concentration ~3 mg/mL. (FIG. 2).

Figure 4:
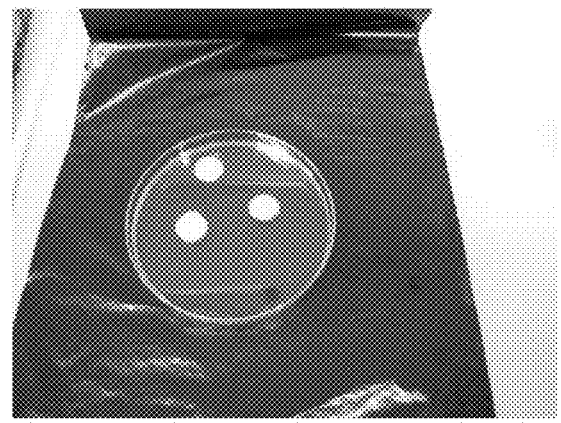
Figure 4:
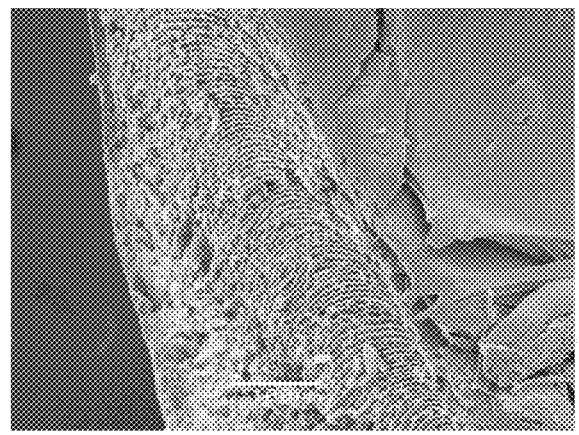

The collagen (acid-soluble) obtained by dialysis is macroscopically inhomogeneous (FIG. 2A) and the size of the fibres is inhomogeneous (FIGS. 2B to 2D). On the other hand, the fibrillated collagen obtained by the method according to the invention is macroscopically homogeneous (FIG. 4A) and the size of the fibres is also homogeneous (FIGS. 4B to 4D).

EXAMPLE 2: IMPLANTATION TRIALS 2.1. Procedure
2.1.1. Implantation of the Dense Matrices All the procedures used are in accordance with the INSERM animal experimentation regulation and ethics committees (Registration No. 006235, Ministry of Agriculture, France).

Figure 5:
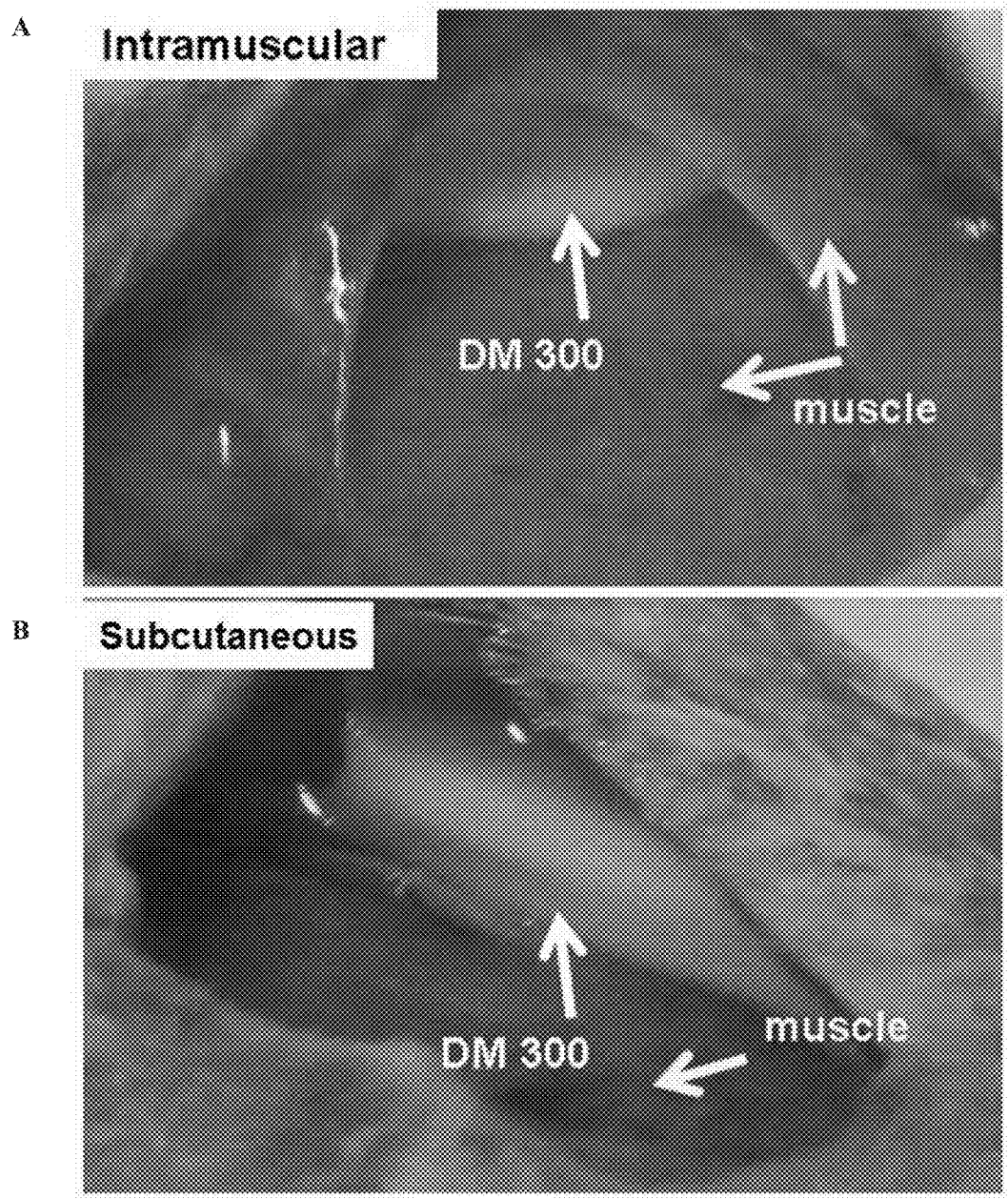
FIG. 5 illustrates the intramuscular (A) and subcutaneous (B) implantation of the dense matrices at 300 mg/mL.
Figure 6:
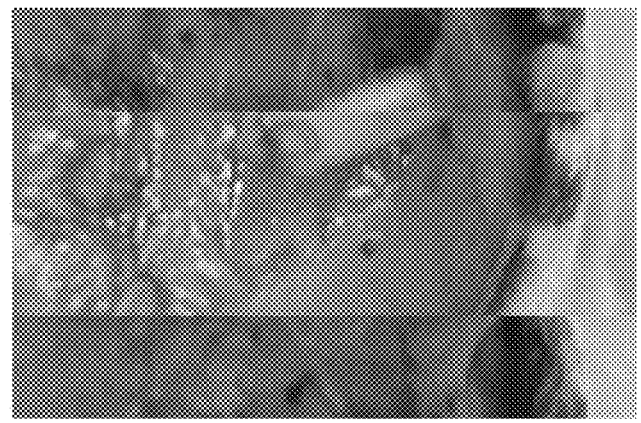
FIG. 6 illustrates the macroscopic appearance of dense matrices at 20 mg/mL (DM 20 FIG. 6A) and 40 mg/mL (DM 40 FIG. 6B) 15 days after intramuscular implantation.
Figure 6:
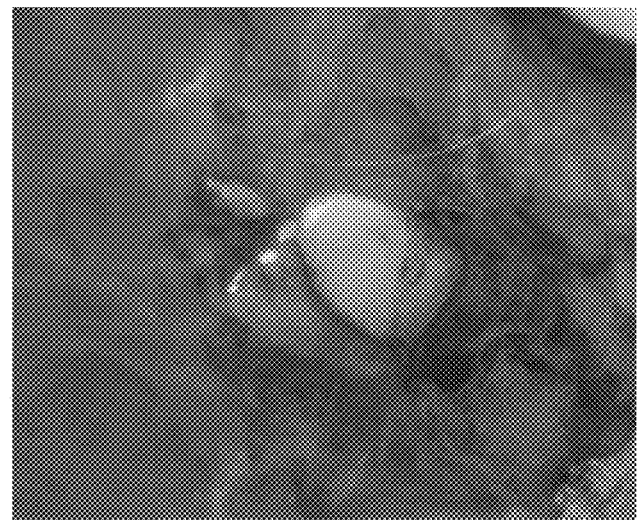

Wistar rats weighing 250 g ((Wi/Wi, Charles-Rivers France) are anaesthetized using a sodium pentobarbital solution (30 mg/kg, Centravet France). The abdomen is shaved and disinfected, and a mid-line laparotomy is performed. Two pockets are produced on either side of the mid-line: one subcutaneous, the other intramuscular. The dense collagen matrices of concentrations varying from 40 to 300 mg/mL are then implanted. The pocket in the muscle is reclosed, then the skin (Vicryl® 4/0). See FIG. 5. Fifteen, thirty or sixty days after the implantation, the rats are euthanized using an excess of sodium pentobarbital and the DMs are explanted and fixed in 4% paraformaldehyde (Merck France). The samples are then embedded in paraffin.

The matrices can be easily handled without tearing.

2.1.2. Histological Analysis

Series of 7 µm sections are produced then stained with hematoxylin-eosin or Masson's trichrome. After observation (Nikon E600 POL microscope) and analyses of the sections photographs are taken (CCD camera, Nikon).

Immunohistological studies were carried out on these sections and the different tissue remodelling elements were demonstrated (macrophages, inflammation control, endothelial cells, neovascularization or vascularization).

2.2. Results

These are given in FIGS. 6 to 12

The implantation of the dense matrices causes no severe reaction to foreign bodies after 15 days of implantation of matrices at 20 and 40 mg/mL (FIGS. 6A and 6B).

15 and 30 days after subcutaneous implantation of a dense matrix at 300 mg/mL, the size of the sample has not varied. 30 days after intramuscular implantation the volume of the sample is similar overall. It is necessary to wait 60 days from implantation in order to visualize a difference (not shown).

Figure 7:
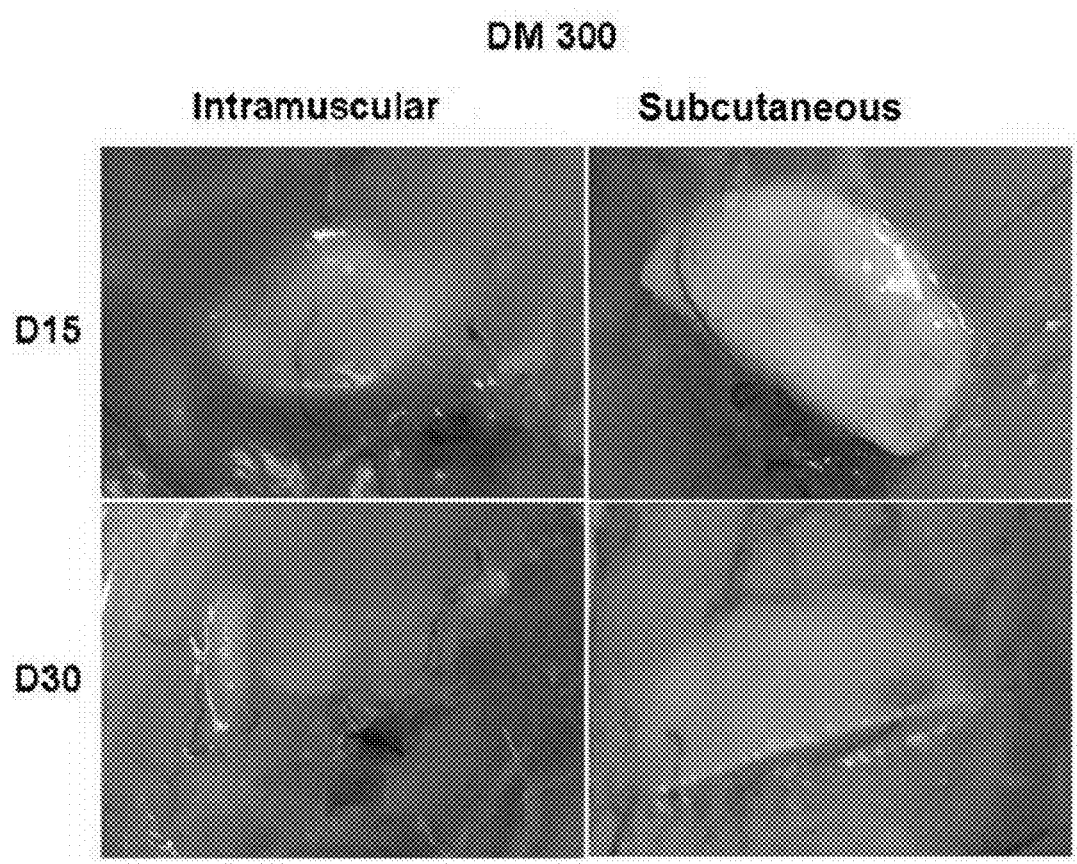
FIG. 7 represents the macroscopic appearance 15 and 30 days after implantation of a dense matrix at 300 mg/mL (DM 300).
Figure 8:
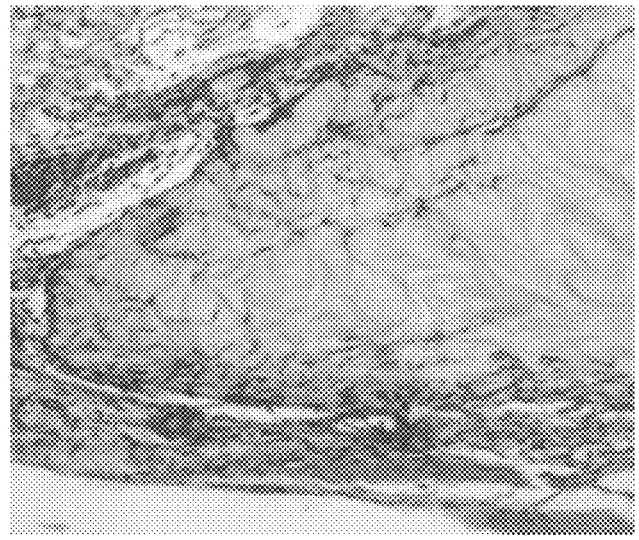
FIG. 8 represents the microscopic appearance of dense matrices at 20 mg/mL (DM 20 FIG. 8A) and 40 mg/mL (DM 40 FIG. 8B) 15 days after subcutaneous implantation.
Figure 8:
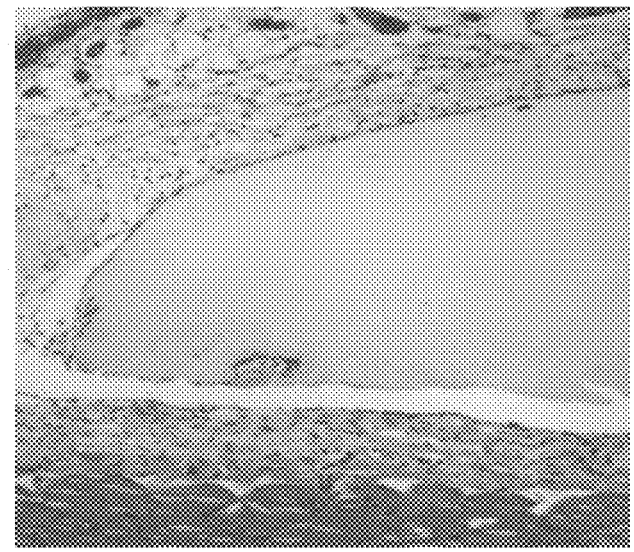

The absence of inflammatory reaction at the site of implantation of a matrix at 300 mg/mL is also noted (FIG. 7).

The rate of colonization of the implants by cells in vivo depends on the collagen concentration. The higher the concentration is the slower the rate. The thicker the matrix is the more time-consuming the colonization within the material.

15 days after implantation, the dense matrix at 20 mg/mL (DM20) is colonized by the fibroblast cells (FIG. 8A). For the dense matrix at 40 mg/mL (DM40), at the level of the external edge a few facing cells are observed and begin to migrate inside the gel (FIG. 8B).

Figure 9:
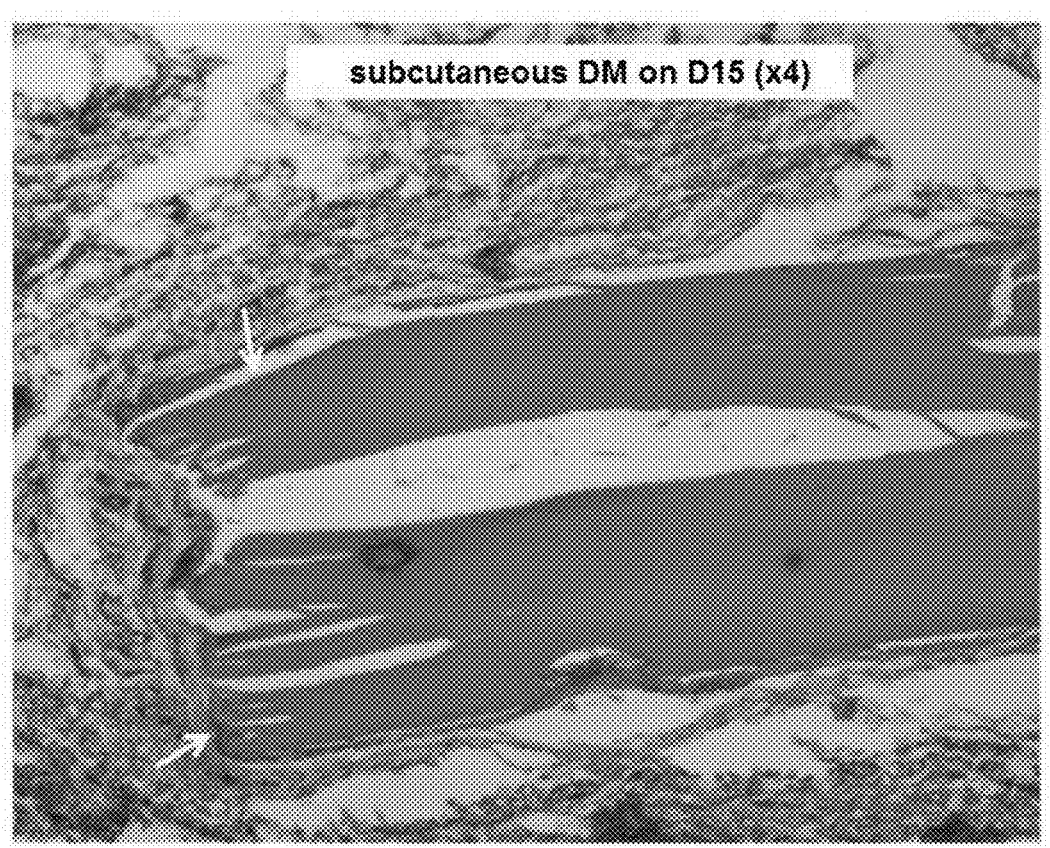
FIG. 9 represents the microscopic appearance 15 days after subcutaneous implantation of a dense matrix at 300 mg/mL (DM300) at 4× magnification. The arrows represent the cells which migrate/colonize inside the gel.
Figure 10:
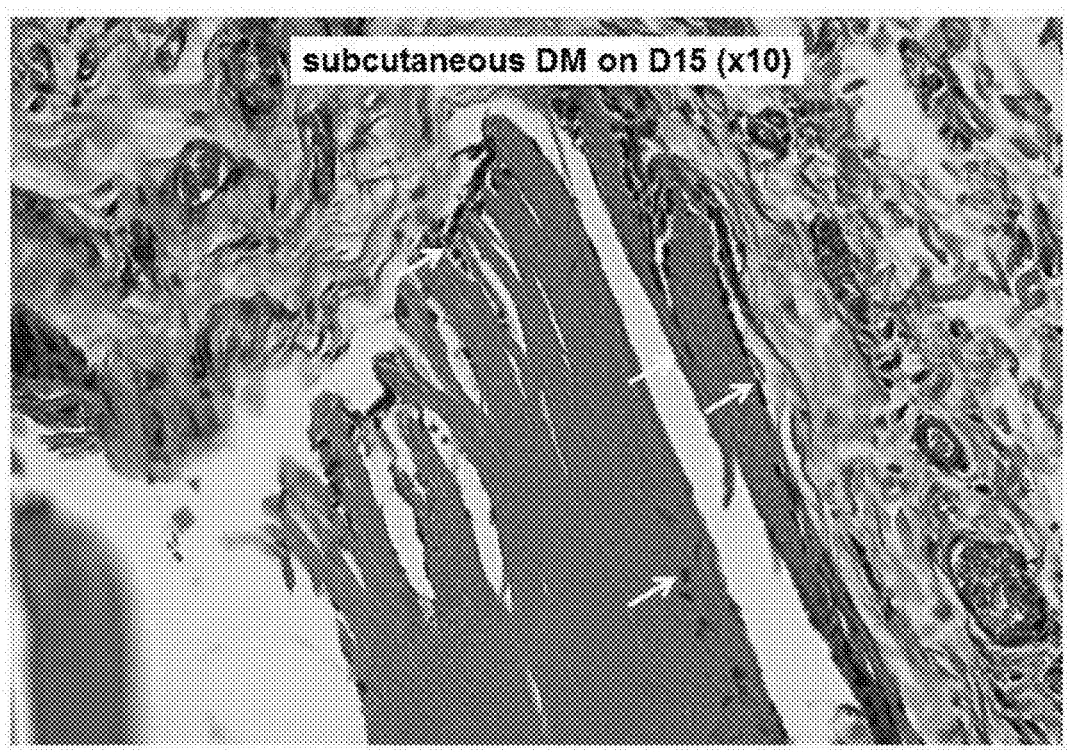
FIG. 10 represents the microscopic appearance after 15 days of subcutaneous implantation of a dense matrix at 300 mg/mL (DM300) at 10× magnification. The arrows represent the cells which migrate inside the gel.

Subcutaneously, and generally for concentrations of 300 mg/mL (DM 300), cell colonization takes place more towards the cutaneous surface than towards the muscle fascia. The DM300 is surrounded by a fine capsule. At the external edge a few facing cells are observed and begin to migrate inside the gel (FIGS. 9 and 10).

Figure 11:
FIG. 11 represents the microscopic appearance after 15 days of intramuscular implantation of a dense matrix at 300 mg/mL (DM300) at 4× magnification. The arrows represent the cells which migrate inside the gel.
Figure 12:
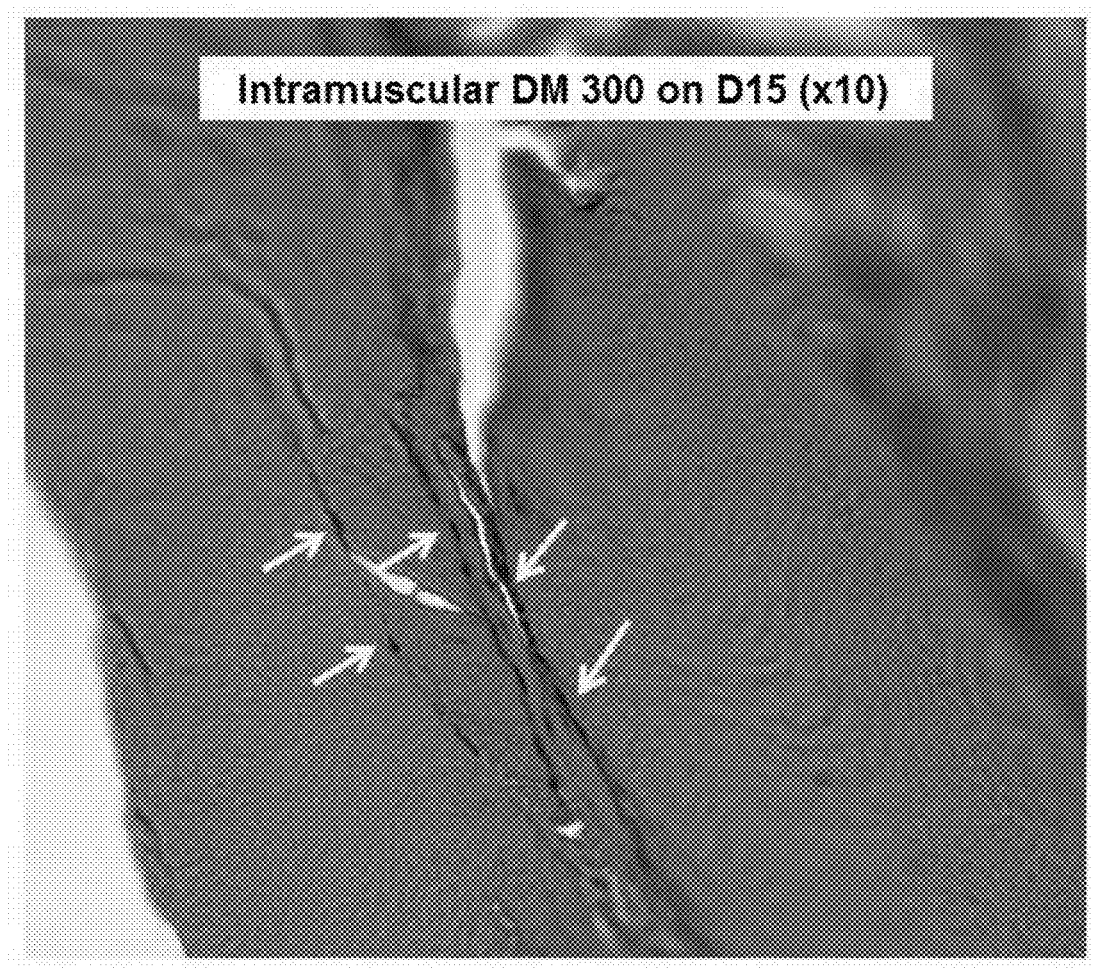
FIG. 12 represents the microscopic appearance after 15 days of intramuscular implantation of a dense matrix at 300 mg/mL (DM300) at 10× magnification. The arrows represent the cells which migrate inside the gel.

The shift between the results after subcutaneous and intramuscular implantation is normal. The intramuscular cicatrization is more rapid due to the local vascularization (FIGS. 11 and 12).

The applications can therefore be extremely varied depending on the type of dense matrix selected and the implantation site.

The invention claimed is:

1. A method for preparing a homogeneous collagen-based material, said method comprising the following stages:
   a) preparing an acid solution of pure collagen having a concentration between 0.01 and 5 mg/mL in an aqueous solvent,
   b) continuously injecting the acid solution of pure collagen by controlled pressure means using a rate of injection comprised between 1 and 15 µl/min which is adapted so that the pressure force on both sides of the membrane is identical, into a dialysis cell having at least one end that is closed by a dialysis membrane with a fixed porosity, said membrane being in contact with a polymer solution in an acid medium, wherein the solvent, as well as acid and ions present in the acid solution of pure collagen, diffuse through said membrane and into the polymer solution in an acid medium, the concentration of which is adapted to the final collagen concentration,
   c) optionally interrupting the injection of the acid solution of pure collagen in order to reach equilibrium or have different continuous concentration layers,
   d) keeping the acid solution of pure collagen, the dialysis cell and the polymer solution in an acid medium under conditions allowing the selective mass transfer of the solvent, acid, and ions from the collagen in order to concentrate the acid solution of pure collagen and form a pure homogeneous collagen-based material having a collagen concentration of 5 to 1000 mg/ml in the dialysis cell or on the surface of the dialysis membrane, and
   e) recovering the dialysis cell in which the homogeneous collagen-based material is contained or of the membrane on the surface of which the homogeneous collagen-based material is fixed, and
   f) forming fibrils from the pure homogeneous collagen-based material, before or after stage e) by immersion of the collagen material under ammonia vapor.

2. The method according to claim 1 wherein the ions are mineral phase precursors selected from the group consisting of calcium and phosphate salts.

3. The method according to claim 1, wherein the polymer is polyethylene glycol the molecular weight of which is greater than 3000 Da.

4. The method according to claim 1 wherein the fibrils are formed by treatment of the material based on homogeneous pure collagen by a gas (basic) or liquid (neutral or basic) phase.

5. The method according to claim 1, wherein the acid solution of pure collagen used in stage a) has a collagen concentration between 0.5 and 3 mg/mL.

6. The method according to claim 1 wherein the concentration of the pure homogeneous collagen-based material obtained is 5 to 250 mg/mL.

7. A method for preparing a homogeneous collagen-based material, said method comprising the steps of:
continuously injecting using a rate of injection between 1 and 15 µl/min which is adapted so that the pressure force on both sides of the membrane is identical an acid solution of collagen comprising pure collagen, having a concentration between 0.01 and 5 mg/mL acid and an aqueous solvent into a dialysis cell, the dialysis cell comprising at least one membrane surface in contact with a polymer solution comprising a polymer in an acid medium, the at least one membrane surface having a porosity sized to prevent diffusion,
optionally interrupting the injection of the acid solution of pure collagen in order to reach equilibrium or have different continuous concentration layers, of the pure collagen and the polymer across the at least one membrane surface,
maintaining the polymer solution at an osmotic pressure greater than an osmotic pressure of the acid solution of collagen to promote diffusion of the acid and aqueous solvent through the at least one membrane surface into the polymer solution to form, within the dialysis cell, a homogeneous pure collagen-based material having a collagen concentration of 5 to 1000 mg/ml, and
recovering the homogeneous pure collagen-based material having a collagen concentration of 5 to 1000 mg/ml from the dialysis cell, and
forming fibrils in the homogeneous pure collagen-based material having a collagen concentration of 5 to 1000 mg/ml before or after said material is recovered from the dialysis cell by immersion of the collagen material under ammonia vapor.

8. The method according to claim 7, wherein the acid solution of collagen further comprises mineral phase precursors selected from the group consisting of calcium and phosphate salts, and the mineral phase precursors diffuse through the at least one membrane surface into the polymer solution.

* * * * *